United States Patent

Shimodaira et al.

[11] Patent Number: 5,910,007
[45] Date of Patent: Jun. 8, 1999

[54] BUCCAL TUBE

[75] Inventors: Kenichi Shimodaira; Junichi Hayashi; Michio Ito, all of Nagano-ken, Japan

[73] Assignees: Injex Corporation; Matsumoto Dental College, both of Nagano-ken, Japan

[21] Appl. No.: 08/899,548

[22] Filed: Jul. 24, 1997

[30] Foreign Application Priority Data

Jul. 25, 1996 [JP] Japan .................................. 8-196785

[51] Int. Cl.⁶ ...................................................... A61C 3/00
[52] U.S. Cl. .............................................................. 433/17
[58] Field of Search ............................. 433/8, 9, 10, 11, 433/12, 13, 14, 15, 16, 17

[56] References Cited

U.S. PATENT DOCUMENTS

| | | | |
|---|---|---|---|
| 5,203,804 | 4/1993 | Nikutowski et al. | 433/8 |
| 5,383,784 | 1/1995 | Serentz | 433/8 X |
| 5,573,401 | 11/1996 | Davidson et al. | 433/8 X |
| 5,613,849 | 3/1997 | Tanaka et al. | 433/8 |

*Primary Examiner*—Nicholas D. Lucchesi
*Attorney, Agent, or Firm*—Hill & Simpson

[57] ABSTRACT

A buccal tube has a base part and at least one tube, and it is formed from a metal material comprising Ti or Ti alloy, using a metal injection molding method. The buccal tube can be formed from a metal material which contains Ti as a base component, from 0.03 to 0.5 wt % C, from 0.08 to 0.8 wt % O and from 0.03 to 0.6 wt % N. The total C, O and N content in the metal material is preferably from 0.14 to 1.1 wt %. Furthermore, pores of average diameter from 0.5 to 50 μm are preferably dispersed in at least a surface region of the buccal tube, and the porosity of the holes is preferably from 0.05 to 5.0 vol %. The buccal tube may further comprises at least one engaging part which is preferably formed into a hook or engaging piece for example.

20 Claims, 4 Drawing Sheets

BUCCAL TUBE

BACKGROUND OF THE INVENTION

1. Field of the Invention

The invention relates to a buccal tube which is used in orthodontic treatment or the like.

2. Description of the Prior Art

As for dental appliances which are used in the oral cavity, there are known brackets (tie wings), wires for pulling the brackets and buccal tubes which are to be fixed to the molars while pulling the ends of the wires, which are used for correcting tooth alignment.

A buccal tube includes one or two tubes into which wires or inner wires of a facebow are inserted, and a fixing platform which is to be fitted to a ring-like fixing part which is to be fitted onto a molar, and these are formed of a metal material and formed into an integral body.

Since such buccal tubes are small and have a complex shape, they have been so far manufactured with the lost-wax method, and in that method stainless steel is used mainly as the metal material therefore.

However, stainless steel buccal tubes have less bio-compatibility, and in particular they have adverse effects to living bodies such as causing the onset of metal allergies and cancer as a result of the dissolution of Ni and Cr. Furthermore, the visual image or esthetics when the brackets are fitted are poor because of the surface metallic luster thereof.

Further, stainless steel buccal tubes which have been made using the lost-wax method are liable to have defects such as pinholes, and so there are problems in that they have low strength and ununiformity in their qualities, and the manufacturing yield is poor.

SUMMARY OF THE INVENTION

The object of the present invention is to provide a buccal tube having improved characteristics.

In order to achieve the object, the present invention is directed to a buccal tube which comprises a base part and at least one tube, wherein they are formed from a metal material comprising Ti or Ti alloy.

According to the invention described above, it is possible to provide a buccal tube which is light and has high strength and hardness, which is not liable to be deformed and damaged and which has excellent durability and corrosion resistance. Further, the buccal tube has excellent bio-compatibility, and has less metallic luster so that esthetics or visial image is not lowered even when it is fitted.

Further, in order to achieve the object, the present invention is also directed to a buccal tube which comprises a base part and at least one tube, wherein they are formed from a metal material which contains Ti as a base component, from 0.03 to 0.5 wt % of C, from 0.08 to 0.8 wt % of O and from 0.03 to 0.6 wt % of N.

According to the invention described above, it is possible to provide a buccal tube which has physical properties such as ideal strength and hardness, ductility (toughness) and elasticity and the like in addition to the above advantages.

Furthermore, in order to achieve the object, the present invention is also directed to a buccal tube which comprises a base part and at least one tube, wherein they are manufactured into an integral body using a metal injection molding method, and they are formed of a metal material which contains Ti as a base component, from 0.03 to 0.5 wt % of C, from 0.08 to 0.8 wt % of O and from 0.03 to 0.6 wt % of N.

According to the invention described above, it is possible to manufacture a buccal tube in good production yields even if it has a fine and complicated shape, and it is also possible to provide a buccal tube which has physical properties such as ideal strength and hardness, ductility (toughness) and elasticity and the like. Further, the buccal tube of this invention has excellent bio-compatibility, and has less metallic luster so that esthetics or visial image is not lowered when it is fitted.

In these inventions, it is preferred that the total content of C, O and N in the metal material is from 0.14 to 1.1 wt %. This enables to maintain the strength and ductility of the metal material at a desired level.

Further, in these inventions, it is also preferred that pores of average diameter from 0.5 to 50 $\mu$m are dispersed in at least a surface region of said buccal tube.

By constructing the buccal tubes in this way, it becomes possible to improve the wettability of the surface of the buccal tubes, so that moistness for body tissues such as the mucous membrane in the oral cavity is assured. Further, it is also possible to prevent that food will be retained in the open pores in use thereby causing the propagation of microorganisms. Furthermore, since the luster is suppressed by the presence of the pores, this also contributes to improvement of the visual image or esthetics when it is fitted.

In this case, it is further preferred that the porosity of said pores is from 0.05 to 5.0 vol %. According to the adoption of this range of the porosity, it becomes possible to further improve the wettability of the surface of the buccal tubes without lowering the strength and ductility of the metal material.

Further, in the present inventions, it is also preferred that the buccal tube further includes engaging part such as a hook or an engaging piece.

By providing such engaging part, it is possible to stretch a rubber band or the like to the engaging part to pull a prescribed tooth by the band. Further, it is also possible to tie a wire thereto, so that dental appliances for correcting teeth alignment such as wires can be easily attached and fixed thereto.

DETAILED DESCRIPTION OF THE PREFERRED EMBODIMENTS

A buccal tube of the present invention is described in detail below on the basis of the preferred embodiment shown in the attached drawings.

Figure 4:
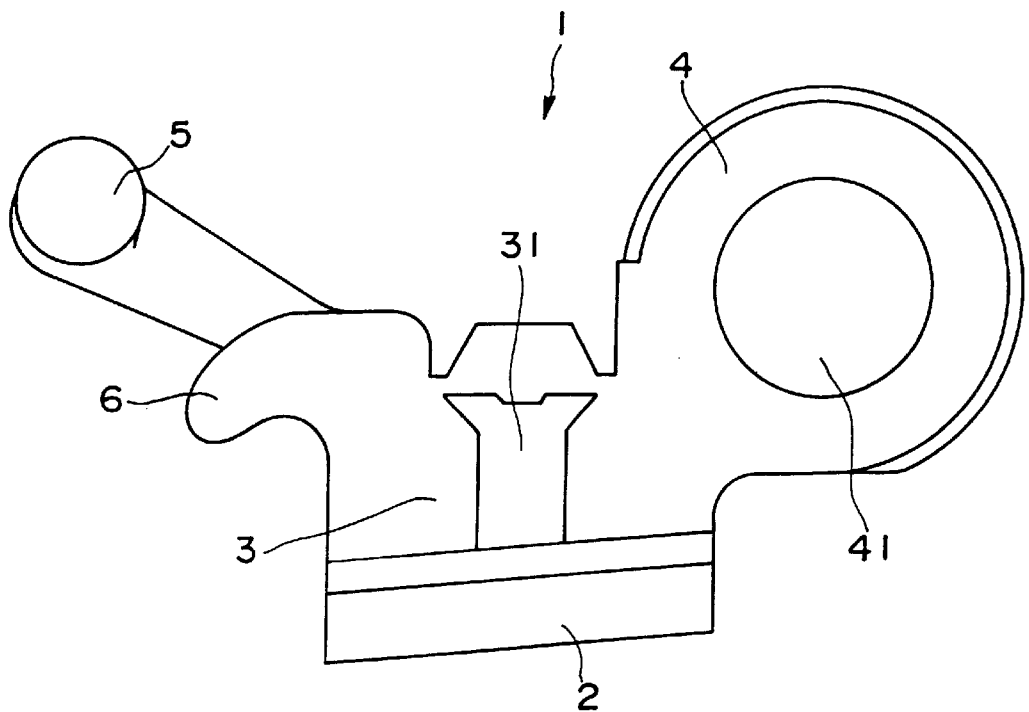
FIG. 4 is a right-side view of an example of a buccal tube according to the present invention.
Figure 5:
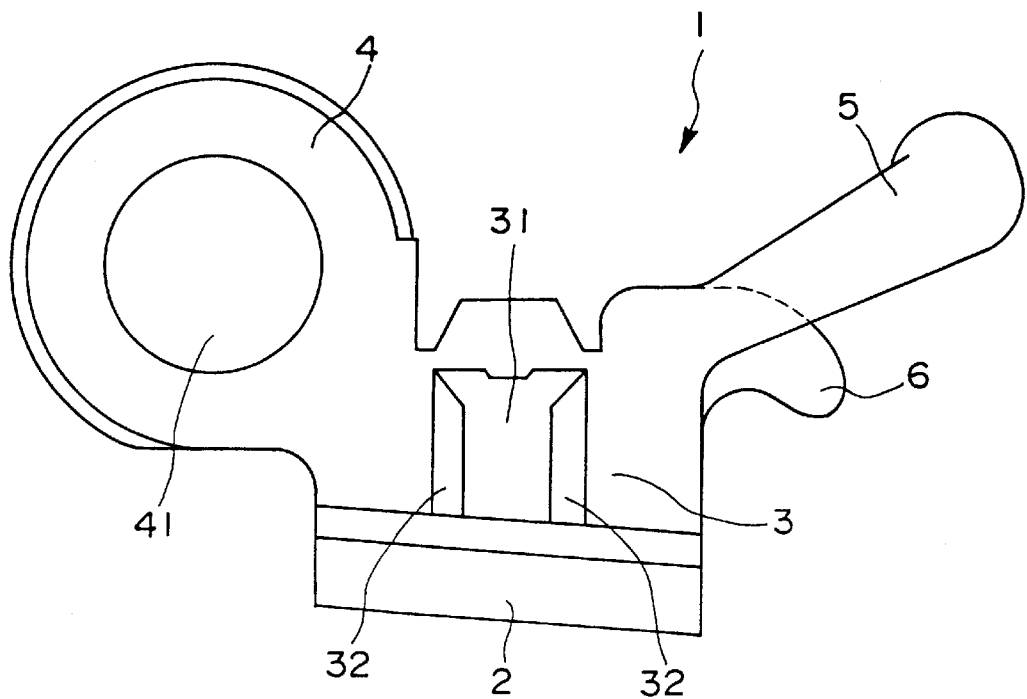
FIG. 5 is a left-side view of an example of a buccal tube according to the present invention.
Figure 6:
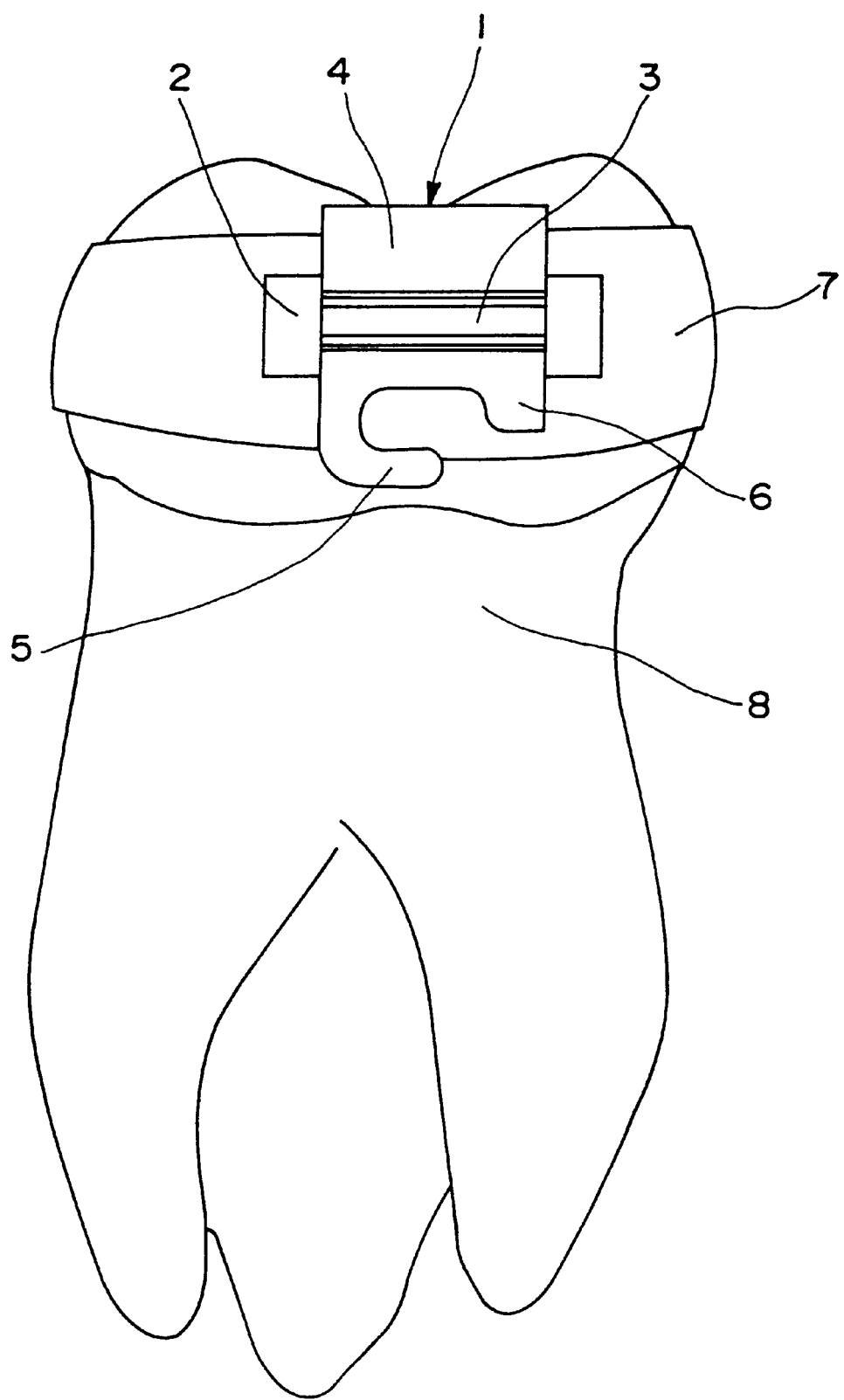
FIG. 6 is an illustration which shows the state where a buccal tube according to the present invention is fixed to a molar.

FIGS. 1, 2, 3, 4 and 5 are respectively a plan view, front view, back view, right-side view and left-side view of an example of a buccal tube of this invention, and FIG. 6 is an illustration which shows the state where a buccal tube of this invention is fixed to a molar.

As shown in these drawings, a buccal tube 1 has a plate-like base part 2, a first tube 3, a second tube 4, a hook (first engaging part) 5 and an engaging piece (second engaging part) 6, which are formed into an integral body. Such a buccal tube is known as a dental appliance used for orthodontic purposes.

The base part 2 is the part which functions as a fixing platform which is to be fixed, for example by welding, soldering or with an adhesive, to a ring-like fixing part 7 which is fitted over the molar 8. This base part 2 is formed with a plate-like part which is curved in a prescribed manner so as to correspond with the curvature the outer surface of the fixing part 7.

Moreover, in order to increase further the fixing strength (and especially the weld strength) of the base part 2 with respect to the fixing part 7, the fixing part 7 is preferably constructed from the metal material of the same type as that of the buccal tube 1 which is described hereinafter.

The first tube 3 is formed on the top of the base part 2. The first tube 3 is formed into a headgear tube, and the ends of a wire (not shown in the drawings) for pulling the brackets for orthodontic purposes are to be inserted into the internal cavity 31 thereof.

As shown in FIGS. 4 and 5, the transverse cross-sectional shape of the internal cavity 31 of the first tube 3 is roughly Y-shaped. Furthermore, the tapered guide surface 32 is formed in the left side end of the first tube 3 (which is shown at the left side in FIG. 1) in order to facilitate insertion of the wire into the internal cavity 31.

The second tube 4 is formed on the side part of the first tube 3. The second tube 4 has an internal cavity 41 into which the end of the internal wire (not shown in the drawings) of a facebow is to be inserted. Here, it is to be noted that the facebow is a device which has a pair of internal and external wires. The internal wire is fitted to the buccal tube while the external wire is pulled with a chin cap or headgear for moving the molar by the pulling force.

The cross-section of the internal cavity 41 of the second tube 4 has a circular shape. Furthermore, the axis of the internal cavity 41 and the axis of the internal cavity 31 have a substantially parallel positional relationship.

The hook 5 is formed so as to protrude from a portion of the first tube 3 which is on the opposite side to the second tube 4 over the axis of the first tube 3. The middle portion of the hook 5 is bent over at roughly right angles so that the tip position of the hook 5 is oriented roughly parallel with the axes of the first tube 3 and the second tube 4.

The hook 5 is used for pulling another prescribed tooth. That is to say, a band made of rubber, for example, is stretched between the hook 5 and an orthodontic bracket which has been fixed to the tooth which is to be pulled and the aforementioned tooth is pulled in the direction of the buccal tube 1 by the tension (elastic force) of the rubber band.

The engaging piece 6 is formed so as to protrude from a side part of the first tube 3 which is positioned on the same side as the hook 5. The engaging piece 6 has a shape which curves toward the base part 2 as shown in FIG. 5. The engaging piece 6 is provided as a means to which the wire is tied up.

The buccal tube 1 as described above is made from a metal material comprising Ti or Ti alloy, and in particular it is preferably made from a metal material which comprises Ti as a base component, from 0.03 to 0.5 wt % of C, from 0.08 to 0.8 wt % of O and from 0.03 to 0.6 wt % of N.

Since Ti or Ti alloys are light in weight and have high strength and hardness, they are not liable to deformation or failure, and they have excellent durability and corrosion resistance. As mentioned earlier, buccal tubes are small parts and have a complex shape, and the protruding parts such as the hook 5 and the engaging piece 6 in particular are liable to damage such as bending, folding (cracking) and flaw and the like. Hence, Ti or Ti alloy which has such properties that are mentioned above is ideal as a structural material for a buccal tube 1.

Further, Ti or Ti alloy has excellent biocompatibility, since there is very little dissolution of the metal component and therefore the onset of metal allergy is also suppressed, for example. Moreover, Ti or Ti alloy has little stainless steel-like metallic luster and so there is no esthetic loss when the buccal tube is being worn.

In the metal material from which the buccal tube 1 is constructed (hereinafter, referred to simply as the "metal material"), the C, O and N are present in the form of compounds with the Ti, for example. By including a good balance of these elements in the metal material, the physical properties such as strength, hardness, ductility (toughness) and elasticity which are particularly desirable for a buccal tube are obtained. Among these elements, the inclusion of N is particularly important. Even when present in trace amounts, N has a great improving effect on the aforementioned physical properties of the metal material.

Hereinbelow, a description is made with regard to the ideal contents of C, O and N in the metal material. However, it is of course to be understood that the composition of the metal material in this invention is not limited to these contents.

The C content in the metal material is preferably 0.03 to 0.5 wt %, more preferably 0.04 to 0.2 wt %, and most preferably 0.05 to 0.1 wt %. If the C content is less than 0.03 wt %, then, in those cases where the O and N contents are low, the strength of the metal material is reduced. On the other hand, if the C content exceeds 0.5 wt %, then the ductility of the metal material is reduced.

The O content in the metal material is preferably 0.08 to 0.8 wt %, more preferably 0.1 to 0.5 wt %, and most preferably 0.25 to 0.3 wt %. If the O content is less than 0.08 wt %, then, in those cases where the C and N contents are low, the strength of the metal material is reduced. On the other hand, the O content exceeds 0.8 wt %, then the ductility of the metal material is reduced.

The N content in the metal material is preferably 0.03 to 0.6 wt %, more preferably 0.035 to 0.14 wt %, and most preferably 0.04 to 0.05 wt %. If the N content is less than 0.03 wt %, then, in those cases where the C and O contents are low, the strength of the metal material is reduced. On the other hand, if it exceeds 0.6 wt %, then the ductility of the metal material is reduced.

The total C, O and N content in the metal material is preferably 0.14 to 1.1 wt %, more preferably 0.18 to 0.8 wt %, and most preferably 0.3 to 0.4 wt %. If the sum total content is less than 0.14 wt %, then the strength of the metal material is reduced. On the other hand, if it exceeds 1.1 wt %, then the ductility of the metal material is reduced.

Further, other elements, such as Fe, Cr, Pd, Co, Zr, Al, V, Mo, Ca, P and Si for example, may be included unavoidably or intentionally in the metal material within the ranges where they cause no harmful effects such as metal allergy. The addition of these elements contributes to increasing the strength of the metal material. Furthermore, the addition of Fe, Cr, Al, V, Pd, Zr and Co has the effect of reducing the sintering temperature, and the addition of Ca, P and Si has the effect of improving bio-compatibilty. In this case, it is preferred that these elements are present in a form which forms a metal oxide or an alloy or intermetallic compound with Ti.

Furthermore, the content of such elements other than Ti is preferably in total not more than 50 wt %, more preferably not more than 30 wt %, and most preferably not more than 15 wt %. If such elements are present in too large amount, then the relative Ti content is reduced and thereby the aforementioned characteristics of Ti itself are difficult to realize.

Moreover, the composition of the metal material from which the buccal tube 1 is constructed is not limited to the case where it is uniform throughout the whole of the buccal tube. It is acceptable if there may be local differences in composition. For example, the interior and surface regions of the buccal tube 1 may have different metal material compositions, in which the composition in the surface regions may be that described above.

No particular limitation is imposed upon the hardness of the surface of the buccal tube 1, but it is preferred that a Vickers hardness Hv of the surface of the buccal tube 1 is from 200 to 400, and it is more preferred that a Vickers hardness Hv thereof is from 300 to 380. The effects described earlier can be realized more effectively with such a Vickers hardness described above.

Very small pores are present in at least the surface regions of the buccal tube 1. The buccal tube 1 in this example has very small pores which are dispersed uniformly throughout the whole of the metal material.

In this way, the surface of the buccal tube 1 is rendered hydrophilic (given a water retaining function). Thus, as a result of this hydrophilicity, the wettability of the surface is improved, so that when the surface is wet with saliva, for example, this is retained and drying is prevented. Hence, since moistness for body tissues, especially the soft tissues such as the mucous membrane in the oral cavity, is assured, inflammation is prevented, for example, and therefore the person to whom the buccal tube is fitted is protected from pain.

Furthermore, the luster is suppressed by the presence of the pores and this also contributes to improvement of the visual image or esthetics mentioned earlier.

The average size of such pores is preferably from 0.5 to 50 $\mu$m, and more preferably from 5 to 20 $\mu$m. If the average size of the pores is less than 0.5 $\mu$m, then saliva does not enter the pores satisfactorily and the moistness is liable to fall. Furthermore, if the average size of the pores exceeds 50 $\mu$m, then adverse effect appear, e.g. not only hardness and ductility of the metal material is lowered, but also food will be retained in the open pores in use and this causes the propagation of microorganisms.

Furthermore, it is also preferred that the pore sizes of most of the pores, preferably at least 66% of the pores are distributed within the range of from 0.5 to 100 $\mu$m, and more preferably within the range from 5 to 60 $\mu$m. In this case no limitation is imposed upon the function of the distribution curve, and it may be, for example, a Gaussian distribution or a binomial distribution. In this way, the wettability of the surface is even further improved and the esthetics or visual image are also ensured.

Furthermore, the porosity of the pores is preferably 0.05 to 5.0 vol %, and more preferably 0.5 to 2.5 vol %. If the porosity is less than 0.05 vol %, then there is little improving effect on surface wettability. On the other hand, if it exceeds 5.0 vol %, then the mechanical properties such as the strength (especially the tensile strength) and ductility (toughness) of the metal material are adversely lowered.

Such a porosity may be constant in the thickness direction from the surface of the buccal tube 1, or it may fall gradually on proceeding from the surface into the interior, or the metal material have parts where such changes in the porosity are existed. In the latter case, it is possible to improve the wettability of the surface while retaining the strength and ductility of the buccal tube 1 at a higher level.

Such pores can be formed easily when the buccal tube 1 is manufactured using the metal powder injection molding method described hereinafter, and the various conditions concerning the above-mentioned pores can be controlled suitably by setting the manufacturing conditions, such as the type and amount of binder which is added and the baking conditions (for example, the baking temperature, the baking time, and the degree of evacuation and the gas composition in the baking environment).

The buccal tube 1 described above can be manufactured by means of various methods. However, it is particularly preferred that the buccal tube 1 is manufactured by means of a metal powder injection molding (MIM: Metal Injection Molding). Therefore, hereinbelow, a description is made with reference to the Metal Injection Molding.

(1) A metal powder comprising titanium or a titanium alloy and a binder (organic binder) are prepared, and these ingredients are mixed or kneaded by a kneading machine to obtain a compound.

The mean grain diameter of the metal powder is not subject to any particular limitations. However, in normal cases, the diameter is preferably set to about 5 to 60 $\mu$m, and more preferably set to about 10 to 40 $\mu$m.

Examples of binders include polyethylene, polypropylene, ethylene-vinyl acetate copolymers, and other polyolefins; polymethyl methacrylate, polybutyl methacrylate, and other acrylic resins; polystyrene and other styrene-based resins; and polyvinyl chloride, polyamides, polyesters, polyethers, polyvinyl alcohol, copolymers thereof, and various other resins; as well as various waxes, paraffin, and the like. These binders can be used individually or as mixtures of two or more components described above.

It is preferable for the total amount in which such binders are added to be about 4 to 18 wt %, and more preferably about 4 to 10 wt %. If the amount is less than 4 wt %, fluidity is low during molding, thus leading to precluding or impairing injection molding or resulting in a green body with a nonuniform composition. On the other hand, if the amount is greater than 18 wt %, the coefficient of contraction during the baking of the green body obtained by injection molding is increased, thereby tending to lower the dimensional accuracy and to increase the porosity and the C content over the range mentioned above.

Plasticizers, lubricants, antioxidants, debinding accelerators, surfactants, and various other additives may be added as needed in addition to the aforementioned metal powders and binders during compounding.

As for one example of the compounding conditions, a compounding temperature can be in the range from room temperature to about 150° C., and a compounding time can be about 60 to 180 min.

(2) Using the compound obtained in the above-described step (1) or pellets which are obtained by granulating the compound, injection molding is performed by an injection molding machine to obtain a green body having a predetermined shape of a buccal tube 1. In this case, the dimension of each green body is determined by taking shrinkage which will occur after the baking process into account.

As for examples of the injection molding conditions, a material temperature is preferably set to be about 130 to 170° C. and more preferably about 150 to 160° C., an injection pressure is preferably set to be about 300 to 600 kgf/cm$^2$ and more preferably 300 to 400 kgf/cm$^2$ and a mold temperature is preferably set to be 10 to 20° C.

(3) A debinding treatment (binder removal treatment) is carried out for the green body obtained in the above-described step (2). This debinding treatment is accomplished by performing a heat treatment in a nonoxidizing atmosphere such as a vacuum or a reduced-pressure atmosphere (for example, $1\times10^{-1}$ to $1\times10^{-6}$ Torr).

In this case, it is preferred that the heat treatment conditions include a temperature of about 50 to 650° C. and a duration of about 8 to 72 hours, and it is more preferable that they include a temperature of about 60 to 550° C. and a duration of about 12 to 18 hours.

The debinding treatment (binder removal treatment) may be accomplished by eluting out prescribed components from the binder with the aid of prescribed solvents (liquids, gases).

In this connection, it is to be noted that this process (3) may be omitted.

(4) Next, the green body thus obtained is baked to manufacture a metallic sintered compact. Such a baking process can be carried out two more times.

Preferably, the conditions adopted for such baking include are preferably a temperature of about 400 to 1400° C. and a time of about 10 to 26 hours, and more preferably a temperature of about 500 to 1350° C. and a time of about 15 to 18 hours.

In this case, it is preferable for the sintering atmosphere that the sintering is carried out under the nonoxidizing atmosphere, that is, a vacuum or a reduced-pressure atmosphere (for example, $1\times10^{-2}$ to $1\times10^{-6}$ Torr), or in an inert gas such as argon gas or nitrogen gas, or other reducing atmosphere.

(5) The outer surface of a metal sintered compact thus obtained can be polished by shot blasting or honing, or surface treated by etching, wet-plating, vapor deposition, ion plating, sputtering, CVD or thermal spraying for example, as required.

A buccal tube 1 formed from the metal sintered compact is obtained by way of each of the process indicated above.

In a case where a buccal tube 1 is manufactured using a casting method, it is necessary to overcome problems such as casting defects, melt flow and embrittlement due to the oxygen and nitrogen which react during casting. However, there are no such problems with the aforementioned metal powder injection molding method, and an integrated molding can be carried out even with fine and complex shapes, and high strength and high quality products can be manufactured easily and in good yield. Further, the level of dimensional accuracy is also high.

Furthermore, there is an advantage in that the composition of the metal material from which the buccal tube 1 is constructed, and the conditions relating to the pores, such as the pore size and the porosity for example, can be set to the prescribed levels by adjusting the type and amount of binder which is to be added, the conditions of the debinding treatment and the baking conditions, for example.

Furthermore, it is possible to form fine roughness on the surface of the metal material as the sintered skin by using the metal powder injection molding method, and this also contributes to improving the wettability of the surface. The state of this fine roughness can be controlled by selection of the Ti powder, the setting of the molding conditions and the baking conditions.

Moreover, in this example, the buccal tube 1 has the base part 2, the first tube 3, the second tube 4, the hook 5 and the engaging piece 6 which are formed as an integral body at one time using the metal powder injection molding method. However, any of these parts could be manufactured separately, and then they are joined together by welding for example. In this case, the parts which are welded together may be manufactured by means of the metal powder injection molding method or they can be manufactured by means of some other method (for example a casting method).

Furthermore, the shape and structure of the buccal tube is not limited to that shown in the drawings. For example, the buccal tube may be formed into one in which there are Just either the first tube 3 or the second tube 4, or one in which there are no hook 5 and/or engaging piece 6, or one in which there are a plurality of hooks 5 or engaging pieces 6.

As described above, according to the present invention, it is possible to provide a buccal tube which is light in weight and has adequate mechanical strength and hardness, and which is free of defects and has excellent bio-compatibility. Further, the buccal tube is excellent in attachablity to the fixing part, wear resistance, surface wettability and esthetics.

Furthermore, in the case where the buccal tube is manufactured using the metal powder injection molding method, even complex and fine shapes can be manufactured easily and with good dimensional accuracy, and in good yield.

EXAMPLES

Hereinafter, a description is made with reference to actual examples of the buccal tubes according to the present invention.

(Example 1)

A buccal tube having the shape shown in FIGS. 1 to 5 was manufactured in the following way using the metal powder injection molding method.

First, Ti powder of average particle size 19 $\mu$m, and binder and other additives comprising 2.7 wt % ethylene glycidyl methacrylate-vinyl acetate copolymer, 1.6 wt % dibutyl phthalate, 2.7 wt % wax and 2.9 wt % styrene were mixed to obtain a mixture, and then thus obtained mixture was kneaded for 60 minutes in air at 130° C. using a kneading machine to obtain a compound.

Next, this compound was injection molded using an injection molding machine to obtain a green body of a buccal tube 1 having the shape indicated in FIGS. 1 to 5. The molding conditions at this time were as follows: material temperature was 150° C., injection pressure was 400 kgf/cm$^2$ and mold temperature was 25° C.

Next, the thus obtained green body was subjected to a debinding treatment, in which the green body was heated from 70° C. to 460° C. over a period of 15 hours and then maintained at 460° C. for 1 hour under a reduced pressure of $5\times10^{-3}$ Torr, and then cooled to room temperature.

Next, the green body which had been subjected to the debinding treatment was heated from 600° C. to 1300° C. over a period of 15 hours and then baked at 1300° C. for 3 hours under vacuum ($5\times10^{-6}$ Torr), to obtain a buccal tube 1 formed from a metal sintered compact in which Ti is contained as the main component.

The size and dimension for each part of the buccal tube were as follows.

Size of the base part 2:
 Width 2.0 mm×length 5.3 mm×thickness 0.38 mm (radius of curvature of the base R=12 mm)

Size of the inner cavity 31:
 Minimum width 0.6 mm×height 0.8 mm×length 3.5 mm

Opening angle of the guide 32: 60°

Size of the Inner cavity 41:
 Internal diameter 1.2 mm×length 3.5 mm

Size of the hook:
 External diameter 0.7 mm×total length 2.6 mm (bend angle=90°)

Size of the Engaging Piece: 0.8 mm×0.8 mm (bent over towards the base part side)

(Example 2)

A buccal tube was manufactured in the same way as in Example 1 except that the weight of dibutyl phthalate added to as binder was increased to 1.4 wt % and the amount of Ti powder was reduced by this amount.

(Example 3)

A buccal tube was manufactured in the same way as in Example 1 except that the mixing or kneading of the mixture which contains the Ti powder was carried out in a nitrogen-rich atmosphere (nitrogen content 95%, remainder oxygen).

(Example 4)

A buccal tube was manufactured in the same way as in Example 1 except that the debinding treatment was carried out by heating the green body at a final temperature of 550° C. for 60 minutes under a reduced pressure of $1 \times 10^{-1}$ Torr.

(Example 5)

A buccal tube was manufactured in the same way as in Example 1 except that the final baking temperature and the time for which this temperature was maintained in the baking process of the green body which had been subjected to the debinding treatment were changed to 1200° C. and 2.5 hours, respectively.

(Example 6)

A buccal tube was manufactured in the same way as in Example 1 except that the baking atmosphere in the baking process of the green body which had been subjected to the debinding treatment was set to $1 \times 10^{-4}$ Torr (vacuum).

(Example 7)

A buccal tube was manufactured in the same way as in Example 1 except that a Ti—5 wt % Al—4 wt % V alloy powder of average particle size 20 μm was used instead of the Ti powder.

(Example 8)

A buccal tube was manufactured in the same way as in Example 2 except that a Ti—3 wt % Fe—2 wt % Al—2 wt % V alloy powder of average particle size 20 μm was used instead of the Ti powder.

(Example 9)

A buccal tube was manufactured in the same way as in Example 5 except that a Ti—4 wt % Co—2 wt % V—1 wt % Cr alloy powder of average particle size 18 μm was used instead of the Ti powder.

(Example 10)

A buccal tube was manufactured in the same way as in Example 6 except that a Ti—5 wt % Mo—3 wt % Pd—1 wt % Al alloy powder of average particle size 19 μm was used instead of the Ti powder.

(Comparative Example 1)

A buccal tube having the same shape as that in Example 1 was manufactured using completely annealed stainless steel (SUS316L) by carrying out cutting, grinding, and polishing operations thereto.

(Comparative Example 2)

A buccal tube having the same shape as that in Example 1 was manufactured by carrying out the high frequency melting to a raw material of stainless steel (SUS304) and then carrying out casting thereto under reduced pressure according to the lost-wax method.

<Composition of the Metal Material>

The composition of the metal material (C, O and N contents) was analyzed using an analyzing apparatuses EC-12, RO-116 and TN-114 manufactured by LECO CORPORATION for each of the buccal tubes of Examples 1 to 10 and Comparative Examples 1 and 2. The results are shown in Table 1, as follows.

In this connection, the composition of the metal material of Examples 7 to 10 was the same as that of the alloy powered used in these Examples.

<Conditions Relating to Pores>

The surfaces and cross sectional surfaces of the buccal tubes of Examples 1 to 10 and Comparative Examples 1 and 2 were photographed through an electron microscope (magnification of ×500). Then, the pore diameters and distribution thereof as well as the average pore diameter were obtained with reference to each electron micrograph, and the porosity was obtained from the density ratio. The results are shown in the Table 2, as follows.

<Tests>

The buccal tubes of Examples 1 to 10 and Comparative Examples 1 and 2 were evaluated in terms of each of the items 1 to 6 indicated below. The results are shown in the Table 3, as follows.

1. Mechanical Strength (Flex Resisting Strength)
 (Method of Measurement)
 The flex resisting strength was measured in accordance with JIS Z 2203 using flex resistance strength specimens after sintering.

2. Bonding Strength
 (Method of Measurement)
 The bottom surface of the base part of the buccal tube was welded to the outer surface of a ring-like fixing part which had been manufactured by casting using the same material as that of the buccal tube, and then the bonding strength (welding strength) therebetween was measured using a tensile testing machine.

3. Hardness
 (Method of Measurement)
 The Vickers hardness Hv (load 5 grams) of the surface was measured in accordance with JIS Z 2244. In this connection, it is to be understood that a higher surface Vickers hardness indicates superior wear resistance.

4. Extent of Dissolution of Metal Components (Method of Measurement)

A buccal tube was immersed in 0.05% hydrochloric acid solution for 3 months and then the metal ion concentrations in the liquid were estimated by analysis using plasma emission spectroscopy. In this connection, it is to be understood that a smaller extent of dissolution indicates superior bio-compatibility.

5. Surface Wettability (Method of Measurement)

One hundred buccal tubes of the same shape were immersed for 10 minutes in water to which ultrasonic waves (100,000 Hz) were being applied and then they were left to stand under conditions of temperature 60° C. and humidity 50% RH, and the time taken for the surface of the engaging part (the surface of the tie wing) to dry was measured. In this connection, it is to be understood that a longer time indicates superior wettability.

6. Esthetics (Visual image)

(Method of Evaluation)

The extent of the surface metallic luster was assessed visually. The assessment was made in four stages of ⊚, ○ Δ and x in order from that which had the least metallic luster (=the most esthetic).

<Discussion of the Test Results>

Figure 1:
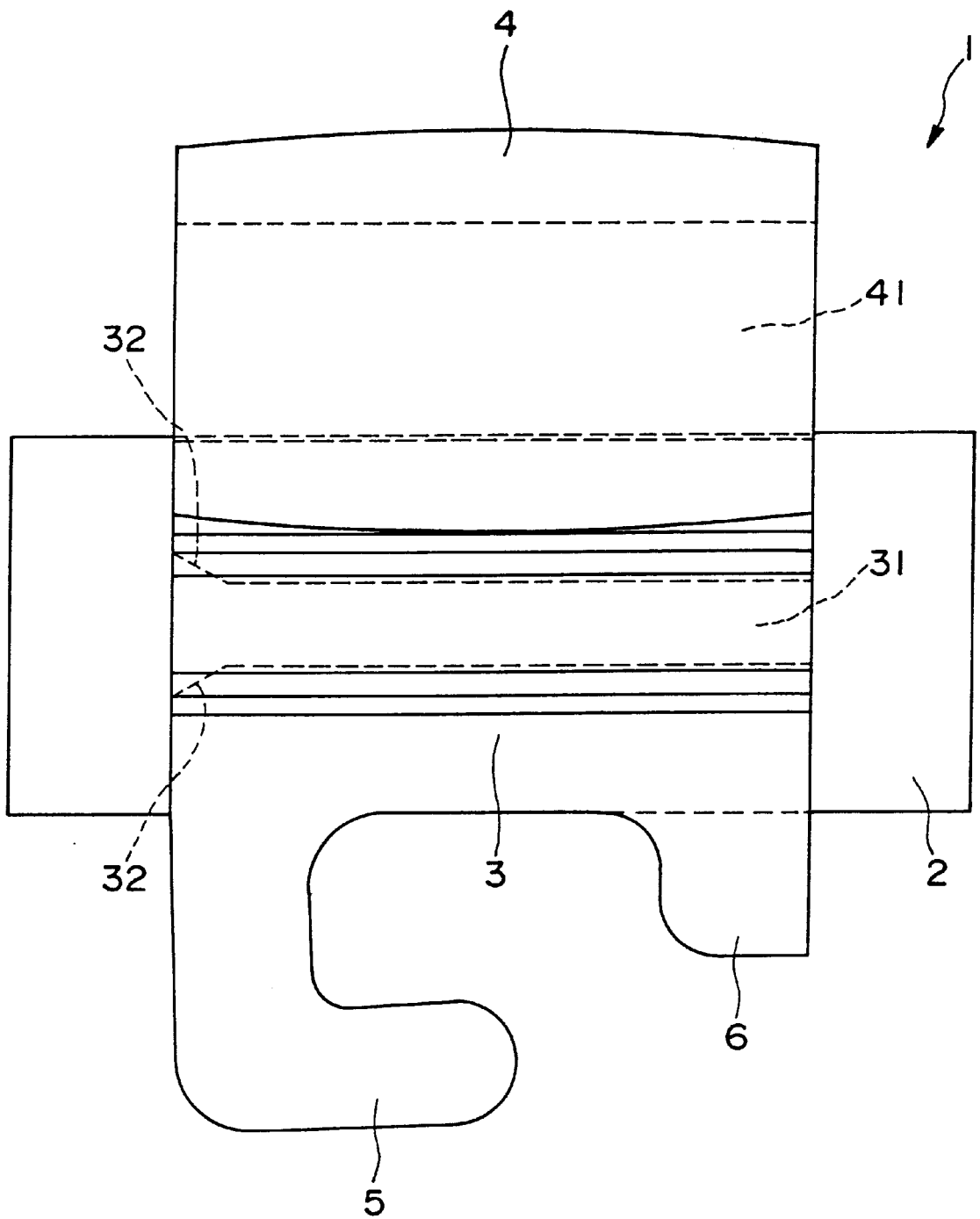
FIG. 1 is a plan view of an example of a buccal tube according to the present invention.
Figure 2:
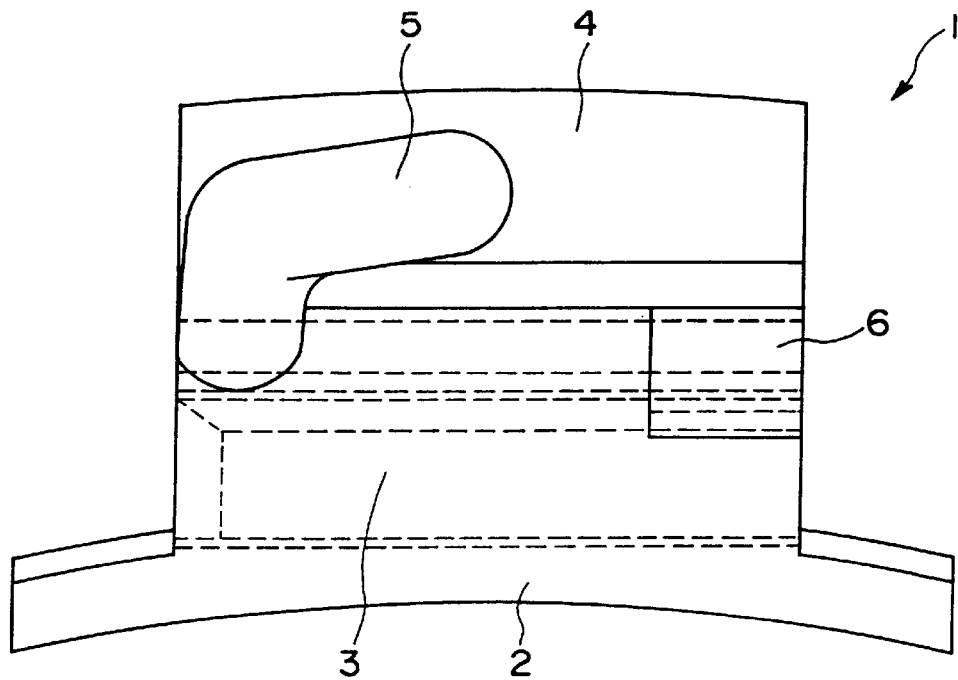
FIG. 2 is a front view of an example of a buccal tube according to the present invention.
Figure 3:
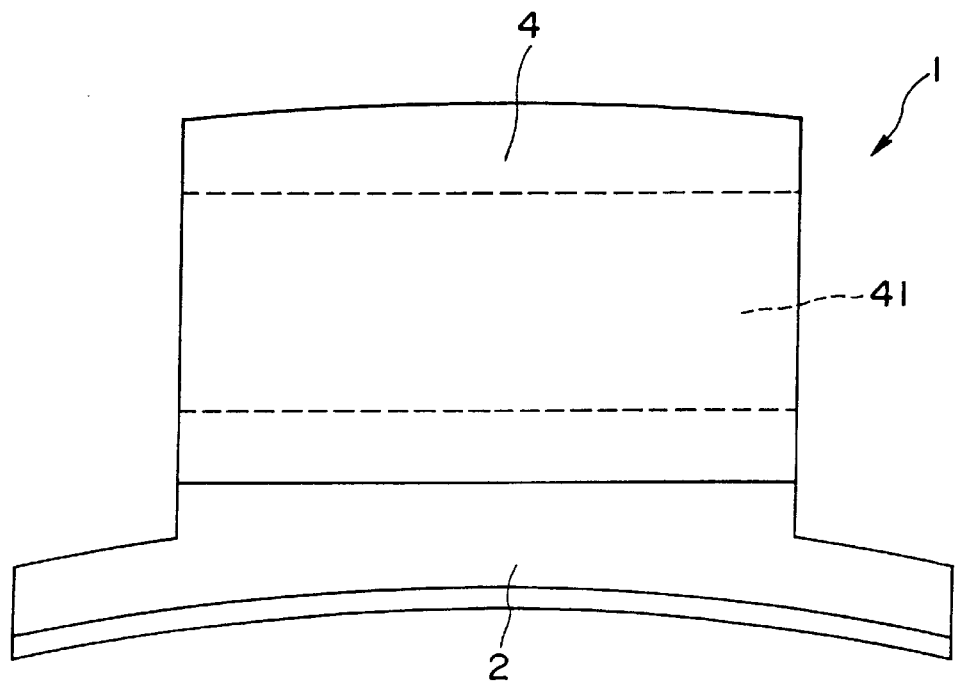
FIG. 3 is a back view of an example of a buccal tube according to the present invention.

As shown in FIG. 3, the buccal tubes of Examples 1 to 10 all had a high mechanical strength (flex resisting strength) and a high bonding strength, and the surface hardness was high and the wear resistance, bio-compatibility and surface wettability were excellent. Further, since they had little metallic luster, they were also esthetically excellent. Furthermore, no defects were seen in any of them, and the quality was excellent.

On the other hand, the buccal tubes of Comparative Examples 1 and 2 had a dense metal structure. Further, since they had virtually no pores, their surface wettability was poor. Furthermore, their bio-compatibility was poor due to the dissolution of Ni and Cr. Moreover, they reflected a lot of light due to their metallic luster, so that they were esthetically poor.

TABLE 1

| | Composition [wt %] | | | |
|---|---|---|---|---|
| Metal Material | C contents | O contents | N contents | Total |
| Example 1 | Ti | 0.04 | 0.07 | 0.04 | 0.15 |
| Example 2 | Ti | 0.05 | 0.11 | 0.04 | 0.20 |
| Example 3 | Ti | 0.07 | 0.10 | 0.14 | 0.31 |
| Example 4 | Ti | 0.43 | 0.09 | 0.04 | 0.56 |
| Example 5 | Ti | 0.07 | 0.12 | 0.05 | 0.24 |
| Example 6 | Ti | 0.05 | 0.66 | 0.08 | 0.79 |
| Example 7 | Ti-Alloy | 0.04 | 0.06 | 0.04 | 0.14 |
| Example 8 | Ti-Alloy | 0.03 | 0.06 | 0.05 | 0.14 |
| Example 9 | Ti-Alloy | 0.05 | 0.05 | 0.03 | 0.13 |
| Example 10 | Ti-Alloy | 0.05 | 0.06 | 0.04 | 0.15 |
| Comp.Ex. 1 | SUS316L | 0.02 | 0.003 | — | 0.023 |
| Comp.Ex. 2 | SUS304 | 0.04 | 0.03 | 0.02 | 0.09 |

TABLE 2

| | Distribution of Diameter of pores* [%] | | | | | Average Diameter of pores [μm] | Porosity [%] |
|---|---|---|---|---|---|---|---|
| | ① | ② | ③ | ④ | ⑤ | | |
| Example 1 | 32 | 53 | 12 | 3 | 0 | 12.7 | 0.07 |
| Example 2 | 37 | 53 | 8 | 1 | 1 | 12.9 | 0.09 |
| Example 3 | 5 | 30 | 48 | 15 | 2 | 21.7 | 2.35 |
| Example 4 | 25 | 50 | 20 | 4 | 1 | 17.9 | 2.04 |
| Example 5 | 0 | 6 | 18 | 22 | 54 | 50.1 | 4.77 |
| Example 6 | 1 | 2 | 10 | 61 | 26 | 45.2 | 4.31 |
| Example 7 | 31 | 52 | 14 | 3 | 0 | 12.6 | 0.08 |
| Example 8 | 32 | 51 | 14 | 3 | 0 | 13.0 | 0.07 |
| Example 9 | 31 | 55 | 12 | 2 | 0 | 12.9 | 0.08 |
| Example 10 | 33 | 50 | 12 | 5 | 0 | 12.8 | 0.09 |
| Comp.Ex. 1 | — | — | — | — | — | — | 0.02 |
| Comp.Ex. 2 | — | — | — | — | — | — | 0.04 |

*①: equal to or greater than 0.5 μm and less than 10 μm
②: equal to or greater than 10 μm and less than 20 μm
③: equal to or greater than 20 μm and less than 30 μm
④: equal to or greater than 30 μm and less than 40 μm
⑤: equal to or greater than 40 μm and equal to or less than 50 μm

TABLE 3

| | Flex Resisting Strength [kg/mm²] | Bonding Strength [kg/mm²] | Vickers Hardness Hv | Amount of Dissolution of Metal Composition [ppm] | Surface Wettability [sec] | Metallic Luster |
|---|---|---|---|---|---|---|
| Example 1 | 62 | 26 | 227 | less than 0.1 | 385 | ⊚ |
| Example 2 | 59 | 24 | 241 | less than 0.1 | 396 | ⊚ |
| Example 3 | 79 | 27 | 308 | less than 0.1 | 415 | ⊚ |
| Example 4 | 70 | 27 | 315 | less than 0.1 | 390 | ⊚ |
| Example 5 | 91 | 29 | 262 | less than 0.1 | 533 | ⊚ |
| Example 6 | 88 | 28 | 333 | less than 0.1 | 477 | ⊚ |
| Example 7 | 92 | 33 | 395 | less than 0.1 | 376 | ○ |
| Example 8 | 89 | 34 | 322 | less than 0.1 | 381 | ○ |
| Example 9 | 90 | 33 | 318 | less than 0.1 | 397 | ⊚ |
| Example 10 | 91 | 36 | 338 | less than 0.1 | 366 | ⊚ |
| Comp. Ex. 1 | — | 27 | 158 | 21.60 | 288 | x |
| Comp. Ex. 2 | — | 25 | 195 | 20.31 | 265 | Δ |

Finally, it is to be noted that the present invention is not limited to the embodiments and the examples described above, and any changes and modifications can be made without departing from the scope and spirit of the present invention which are defined by the following claims.

What is claimed is:

1. A buccal tube, comprising:

a base part; and at least one tube, wherein they are formed from a metal material comprising Ti or Ti alloy, and 0.14 to 1.1 wt % C, O and N.

2. The buccal tube as claimed in claim 1, further comprising at least one engaging part.

3. The buccal tube as claimed in claim 2, wherein said at least one engaging part is formed into a hook.

4. The buccal tube as claimed in claim 2, wherein said at least one engaging part is formed into an engaging piece.

5. A buccal tube, a base part; and at least one tube, wherein they are formed from a metal material comprising Ti or Ti alloy and said buccal tube has a surface region, and pores of average diameter from 0.5 to 50 µm are dispersed in at least said surface region of said buccal tube.

6. The buccal tube as claimed in claim 5, wherein the porosity of said pores is from 0.05 to 5.0 vol %.

7. A buccal tube, comprising:

a base part; and at least one tube, wherein they are formed from a metal material which contains Ti as a base component, from 0.03 to 0.5 wt % of C, from 0.08 to 0.8 wt % of O and from 0.03 to 0.6 wt % of N.

8. The buccal tube as claimed in claim 7, wherein the total content of C, O and N in said metal material is from 0.14 to 1.1 wt %.

9. The buccal tube as claimed in claim 7, wherein said buccal tube has a surface region, and pores of average diameter from 0.5 to 50 µm are dispersed in at least said surface region of said buccal tube.

10. The buccal tube as claimed in claim 9, wherein the porosity of said pores is from 0.05 to 5.0 vol %.

11. The buccal tube as claimed in claim 7, further comprising at least one engaging part.

12. The buccal tube as claimed in claim 11, wherein said at least one engaging part is formed into a hook.

13. The buccal tube as claimed in claim 11, wherein said at least one engaging part is formed into an engaging piece.

14. A buccal tube, comprising:

a base part; and at least one tube, wherein they are manufactured into an integral body using a metal injection molding method, and they are formed of a metal material which contains Ti as a base component, from 0.03 to 0.5 wt % of C, from 0.08 to 0.8 wt % of O and from 0.03 to 0.6 wt % of N.

15. The buccal tube as claimed in claim 14, wherein the total content of C, O and N in said metal material is from 0.14 to 1.1 wt %.

16. The buccal tube as claimed in claim 14, wherein said buccal tube has a surface region, and pores of average diameter from 0.5 to 50 µm are dispersed in at least said surface region of said buccal tube.

17. The buccal tube as claimed in claim 16, wherein the porosity of said pores is from 0.05 to 5.0 vol %.

18. The buccal tube as claimed in claim 14, further comprising at least one engaging part.

19. The buccal tube as claimed in claim 18, wherein said at least one engaging part is formed into a hook.

20. The buccal tube as claimed in claim 18, wherein said at least one engaging part is formed into an engaging piece.

\* \* \* \* \*